United States Patent [19]

Ott

[11] Plant 4,594

[45] Sep. 23, 1980

[54] POINSETTIA

[76] Inventor: Cleveland Ott, 677 Grater Ave., Graterford, Pa. 19426

[21] Appl. No.: 2,260

[22] Filed: Jan. 10, 1979

[51] Int. Cl.[3] ..... A01H 5/00

[52] U.S. Cl. ..... Plt./86

[58] Field of Search ..... Plt./86

*Primary Examiner*—Robert E. Bagwill

*Assistant Examiner*—James R. Feyrer

*Attorney, Agent, or Firm*—Paul & Paul

[57] ABSTRACT

A new and distinct variety of poinsettia plant is a sport of Annette Hegg Hot Pink (U.S. Plant Pat. No. 3,761). The new variety is characterized by bracts which are a lighter pink than the parent and is particularly characterized by venation which is faint and obscure as compared with the more prominent venation of the parent.

1 Drawing Figure

ORIGIN OF THE VARIETY

The new variety of poinsettia plant was discovered by applicant as a sport in a bed of Annette Hegg Hot Pink in applicant's greenhouse near Graterford, Pa. This discovery was made in June, 1978.

ASEXUAL REPRODUCTION OF THE VARIETY

Applicant has asexually reproduced the new and distinct variety in his greenhouse by rooting of cuttings from the new sport. The asexually reproduced poinsettia plants have uniformly new and distinct characteristics.

SUMMARY OF THE VARIETY

The new and distinct variety of poinsettia plant is characterized by the following features:

(1) The bracts are pink, a lighter pink than the parent. The pink color of the bract is deeper with greater illumination and paling with less illumination, as for example, when the bract is shaded. The closest designation on the Royal Horticultural Society (RHS) Color Chart is near 52D when fully illuminated, the color paling when shaded. On the Horticultural Color Chart (HCC) the closest designation is HCC 621 when the bract is fully illuminated, paling to HCC 621/3 when shaded.

(2) The bracts are large and of uniform color. The veins are obscured, particularly on the upper side, by a relatively heavy upper epidermal covering.

(3) The stamen filaments are lighter pink than those of the parent.

BRIEF DESCRIPTION OF THE DRAWINGS

The drawing comprises a photographic reproduction in color of the new and distinct poinsettia plant of this application. The color of the bracts in the photograph is as nearly true as it is reasonably possible to make the same in a color illustration of this character.

DETAILED DESCRIPTION OF THE VARIETY

The new and distinct variety of poinsettia plant of this application was asexually reproduced from a sport of the parent Annette Hegg Hot Pink (U.S. Plant Pat. No. 3,761).

The bracts of the new variety of poinsettia plant are a lighter pink than the parent. The color of the bracts is near HCC 621 when fully illuminated, paling to near HCC 621/3 when shaded. It is believed that the lighter pink color is the result of a heavy white upper layer, and somewhat less heavy white lower layer, of epidermal cells covering a red interior.

The veins in the parent are prominent but in the new variety of plant the veins are almost obscured by the relatively heavy epidermal covering, particularly on the upper side.

The flower of the new variety of plant is larger than the flower of the parent.

The filaments of the stamen are light pink whereas the filaments of the stamen of the parent are dark pink.

The following is a chart which compares the color of the bracts of the new variety of plant of the present application with those of its antecedents and with other pink sports of its antecedents. However, an outstanding distinguishing characteristic of the new variety of plant is that the venation of the bracts is faint and obscure in comparison with the venation of the parent.

Bract Color Comparison with Antecedents and Pink Sports of Antecedents

| Plant Patent No. | Plant Name | Color of Bracts (RHS) No. | (HCC) No. | (HCC) Name |
|---|---|---|---|---|
| (S.N.2259) | Ott | Near 52D | 621 to 621/3 | Carmine Rose |
| (S.N.2260) | Ott | Near 52D | 621 to 621/3 | Carmine Rose |
| 3392 | A.H. Supreme | 45D | 820/2 | Blood Red |
| 2962 | Annette Hegg | 47A | 821/2 | Currant Red |
| 3160 | A.H. Dark Red | 53B | 822/1 | Cardinal Red |
| 3099 | A.H. Pink | Near 47C | 020/2 | Delft Rose |
| 3120 | C-1 Pink | Near 47C | 020/2 | Delft Rose |
| 3738 | C-1 Hot Pink | 47D | 20/2 | Geranium Lake |
| 3761 | A.H. Hot Pink | 52B | 21/1 | Carmine |

Note: A.H. = Annette Hegg

What is claimed is:

1. A new and distinct variety of poinsettia plant, substantially as herein illustrated and described, characterized as to novelty by bracts which are a lighter pink than the parent, Annette Hegg Hot Pink (U.S. Plant Pat. No. 3,761) and characterized particularly by much less prominent veins than the parent, the veins of the new variety being almost obscured by a heavy epidermal covering, particularly on the upper side.

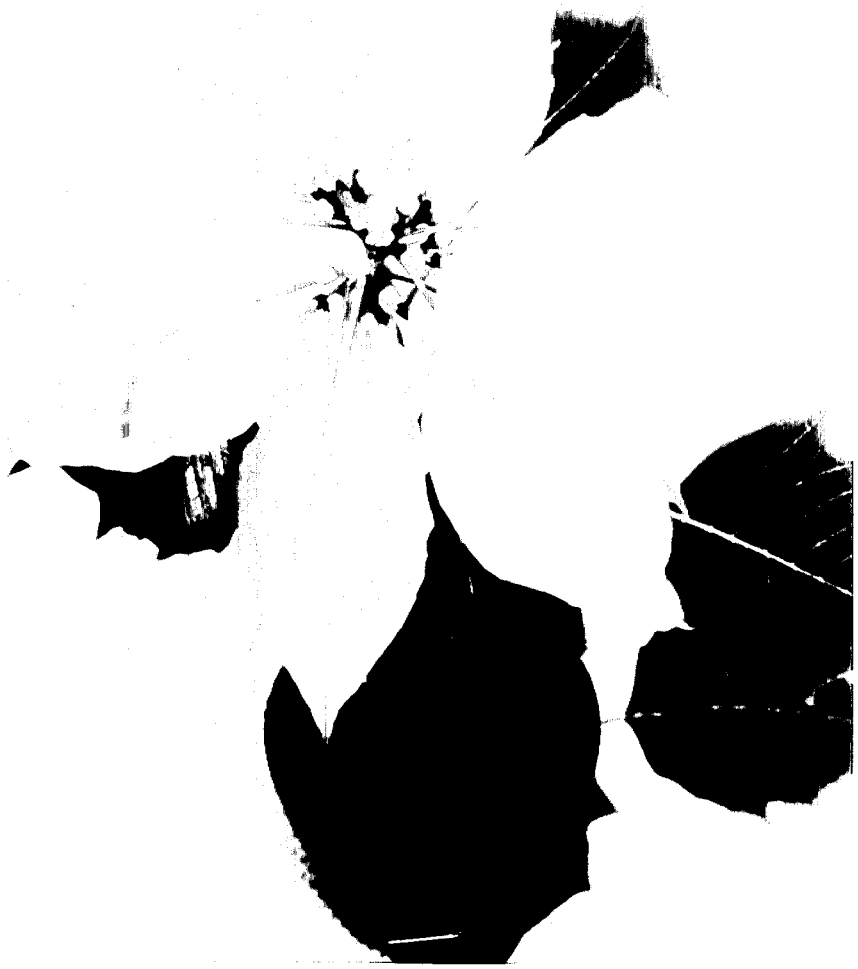

* * * * *